United States Patent
Miyakawa et al.

(10) Patent No.: US 10,307,782 B2
(45) Date of Patent: Jun. 4, 2019

(54) NOZZLE CLEANING METHOD AND AUTOMATED ANALYZER

(71) Applicant: HITACHI HIGH-TECHNOLOGIES CORPORATION, Tokyo (JP)

(72) Inventors: Takushi Miyakawa, Tokyo (JP); Yukinori Sakashita, Tokyo (JP); Yoshihiro Yamashita, Tokyo (JP); Katsuhiro Kambara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 96 days.

(21) Appl. No.: 14/916,633

(22) PCT Filed: Jul. 24, 2014

(86) PCT No.: PCT/JP2014/069614
§ 371 (c)(1),
(2) Date: Mar. 4, 2016

(87) PCT Pub. No.: WO2015/037339
PCT Pub. Date: Mar. 19, 2015

(65) Prior Publication Data
US 2016/0193622 A1    Jul. 7, 2016

(30) Foreign Application Priority Data
Sep. 12, 2013    (JP) .................................. 2013-189092

(51) Int. Cl.
*B05B 12/12* (2006.01)
*B08B 9/023* (2006.01)
(Continued)

(52) U.S. Cl.
CPC ............ *B05B 15/555* (2018.02); *B05B 12/12* (2013.01); *B08B 9/023* (2013.01); *B08B 9/0323* (2013.01);
(Continued)

(58) Field of Classification Search
CPC ... B05B 15/025; B05B 15/0258; B08B 9/032; B08B 9/0323; B08B 9/035
See application file for complete search history.

(56) References Cited

U.S. PATENT DOCUMENTS

2004/0063185 A1* 4/2004 Krupka ............ G01N 35/00594
435/183
2011/0017238 A1* 1/2011 Kuroda ..................... B08B 3/04
134/22.11
(Continued)

FOREIGN PATENT DOCUMENTS

JP    2005-241442 A    9/2005
JP    2008-202945 A    9/2008
(Continued)

OTHER PUBLICATIONS

International Search Report of PCT/JP2014/069614 dated Oct. 28, 2014.
(Continued)

*Primary Examiner* — Mikhail Kornakov
*Assistant Examiner* — Natasha N Campbell
(74) *Attorney, Agent, or Firm* — Mattingly & Malur, PC

(57) ABSTRACT

The nozzle cleaning method includes the following steps: a first cleaning step in which a pre-pressurization liquid is discharged from a dispensing nozzle in a first cleaning position so as to clean the inside wall thereof and a first cleaning liquid is applied to the outside wall of the dispensing nozzle so as to clean said outside wall; a second cleaning step in which a second cleaning liquid is suctioned into the dispensing nozzle in a second cleaning position so as to clean the inside wall thereof; and a third cleaning step in which the second cleaning liquid is discharged from the dispensing nozzle in a third cleaning position so as to clean the inside wall thereof and a third cleaning liquid is applied
(Continued)

to the outside wall of the dispensing nozzle so as to clean said outside wall.

6 Claims, 8 Drawing Sheets

(51) Int. Cl.
    *B08B 9/032* (2006.01)
    *B05B 15/531* (2018.01)
    *B05B 15/555* (2018.01)
    *G01N 35/10* (2006.01)
    *G01N 35/04* (2006.01)

(52) U.S. Cl.
    CPC ........ *G01N 35/1004* (2013.01); *B05B 15/531* (2018.02); *G01N 2035/0453* (2013.01); *G01N 2035/1025* (2013.01)

(56) References Cited

U.S. PATENT DOCUMENTS

| | | | |
|---|---|---|---|
| 2011/0158848 A1* | 6/2011 | Arima | G01N 35/1004 422/62 |
| 2011/0293474 A1 | 12/2011 | Sugiumura et al. | |
| 2012/0003731 A1 | 1/2012 | Kuroda | |
| 2014/0037503 A1* | 2/2014 | Sakashita | G01N 35/1004 422/81 |

FOREIGN PATENT DOCUMENTS

| | | |
|---|---|---|
| JP | 2010-085097 A | 4/2010 |
| JP | 2010-216876 A | 9/2010 |
| JP | 2011-257248 A | 12/2011 |
| JP | 2012-008123 A | 1/2012 |
| WO | 2012/105398 A1 | 8/2012 |

OTHER PUBLICATIONS

International Preliminary Report on Patentability received in corresponding International Application No. PCT/JP2014/069614 dated Mar. 24, 2016.

Extended European Search Report received in corresponding European Application No. 14844189.2 dated Mar. 28, 2017.

* cited by examiner

NOZZLE CLEANING METHOD AND AUTOMATED ANALYZER

TECHNICAL FIELD

The present invention relates to a nozzle cleaning method and an automatic analysis device which include a dispensing nozzle for dispensing a sample and a reagent.

BACKGROUND ART

In particular, in the medical field or the biotechnology field, an automatic analysis device is used which detects a specific biological component, chemical substance or the like contained in a sample such as blood, serum, and urine by causing the sample to react with a reagent. This automatic analysis device needs further improved analysis accuracy in order to achieve a very reliable inspection. For example, when a dispensing nozzle is insufficiently cleaned during a series of analysis-related process, there is a possibility that an adsorbed material remaining in the dispensing nozzle without being completely cleaned may mix with the subsequent sample by being separated from the dispensing nozzle when the subsequent sample is dispensed. This phenomenon is generally called carryover. The carryover affects measurement results.

If a child or an aged person is a patient, only a small amount of the sample can be collected. In addition, in order to ease the burden of the patient or to reduce reagent usage, a trace element of the sample and the reagent may be further progressively used in the future. Therefore, more than ever before, it becomes important to prevent the carryover or contamination in the dispensing process of the sample and the reagent. With regard to a cleaning method for the dispensing nozzle, various methods of using a cleaning solution have been proposed (refer to PTL 1).

CITATION LIST

Patent Literature

PTL 1: Pamphlet of International Publication No. 2012/105398

SUMMARY OF INVENTION

Technical Problem

According to a device disclosed in PTL 1, a dispensing nozzle which has dispensed a reagent is moved to a dispensing nozzle cleaning tank so as to discharge remaining liquid inside a dispensing nozzle. Thereafter, a cleaning solution is aspirated so as to clean an inner wall surface of the dispensing nozzle. The cleaning solution aspirated here is continuously supplied from a supply port, thereby being brought into a state of spilling over (overflowing from) the tank. In this case, an advantageous effect to prevent carryover or contamination can be considerably obtained by aspirating a new cleaning solution in the overflowing state. However, the cleaning solution is consumed more than necessary. The cleaning solution having a high cleaning effect is normally used in cleaning the inner wall surface of the dispensing nozzle. Therefore, if the cleaning solution is uselessly consumed in this way, the cost may increase, and further consumables may be more frequently replaced.

An object of the present invention is to provide a nozzle cleaning method and an automatic analysis device which can prevent carryover or contamination while a cleaning solution is prevented from being uselessly consumed.

Solution to Problem

According to the present invention, in order to achieve the above-described object, an outer wall surface is cleaned before and after an inner wall surface of a dispensing nozzle is cleaned by using a cleaning solution, and the cleaning solution for cleaning the inner wall surface is stored without the cleaning solution overflowing from a storage tank. In this manner, the cleaning solution for cleaning the inner wall surface is prevented from being uselessly consumed.

Advantageous Effects of Invention

According to the present invention, it is possible to prevent carryover or contamination while a cleaning solution is prevented from being uselessly consumed.

DESCRIPTION OF EMBODIMENTS

Hereinafter, embodiments according to the present invention will be described with reference to the drawings.

First Embodiment

1. Automatic Analysis Device

Figure 1:
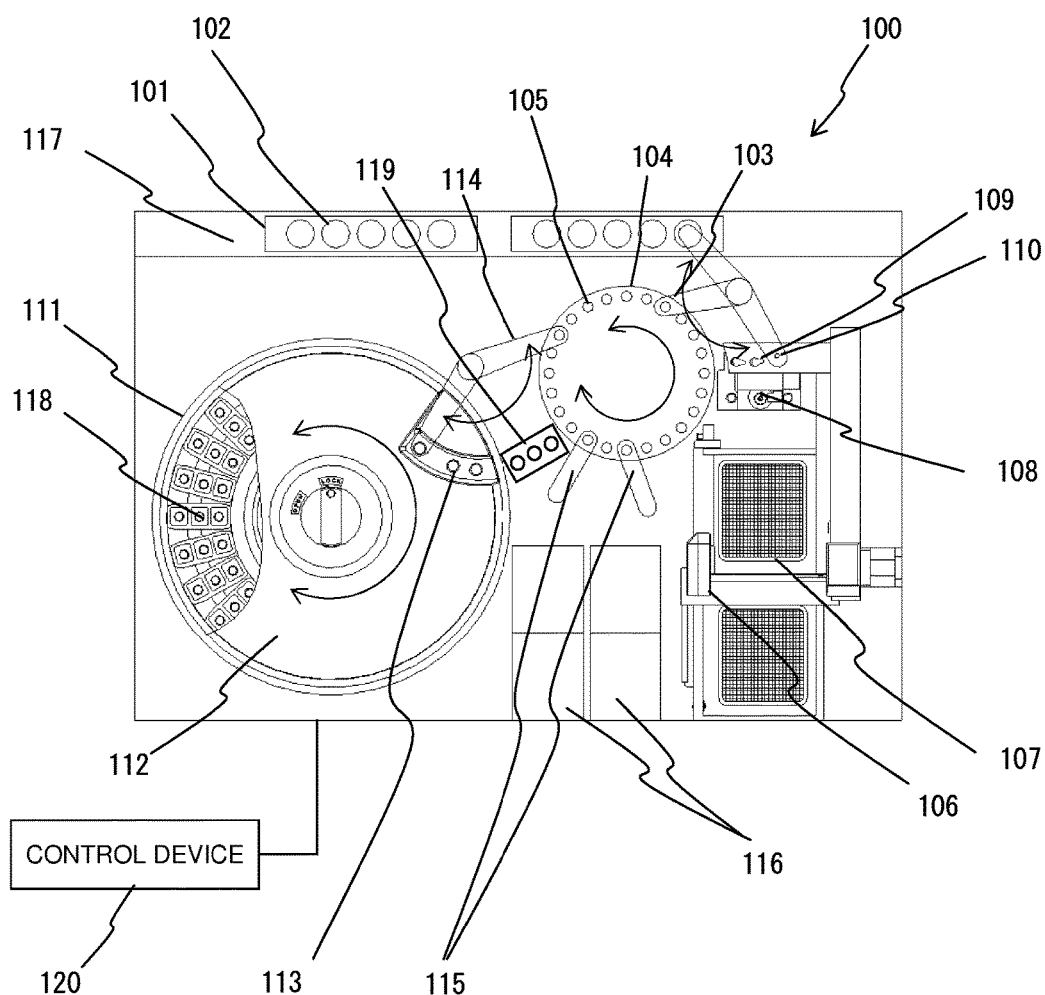
FIG. 1 is a plan view illustrating an overall configuration of an example of an automatic analysis device which is an applicable target of the present invention.

FIG. 1 is a plan view illustrating an overall configuration of an example of an automatic analysis device which is an applicable target of the present invention.

An automatic analysis device 100 includes a rack transporting line 117 for transporting a rack 101, an incubator disc 104 for installing a reaction container 105, a sample dispensing tip-reaction container transporting mechanism 106 for transporting a sample dispensing tip or a reaction container 105, a sample dispensing tip-reaction container holding member 107 for holding the sample dispensing tip or the reaction container 105, a reaction container stirring mechanism 108 for stirring a sample inside the reaction container 105, a sample dispensing device 103 for dispensing and discharging the sample, a reagent disc 111 having a reagent container 118 installed therein, a reagent dispensing device 114 for dispensing and discharging a reagent, a reaction container transporting mechanism 115 for moving the reaction container 105 between the incubator disc 104 and a detection unit 116, the detection unit 116 for detecting a specific biological component or chemical substance contained in a reaction solution inside the reaction container 105, a nozzle cleaning device 119 for cleaning a dispensing nozzle 122 of the reagent dispensing device 114, and a control device 120 for controlling an operation of each device.

The rack transporting line 117 transports the rack 101 to a sample dispensing position of the sample dispensing device 103 on the line. The sample container 102 for holding the sample (specimen) can be installed at multiple locations in the rack 101. In this example, a configuration for transporting the sample by using the line in this way has been described as an example. However, in some cases, a disc-shaped configuration for rotating and transporting the sample may also be adopted.

The incubator disc 104 enables the multiple reaction containers 105 to be installed in an annular shape, and is rotatably driven by a drive device (not illustrated) so as to enable any desired reaction container 105 to move to each predetermined position including the dispensing position of the sample dispensing device 103.

The sample dispensing tip-reaction container transporting mechanism 106 is movable in directions of three axes XYZ, and transports a sample dispensing tip-reaction container to each predetermined location of the sample dispensing tip-reaction container holding member 107, the reaction container stirring mechanism 108, and the incubator disc 104, and between a sample dispensing tip-reaction container discarding hole 109 and a sample dispensing tip mounting position 110.

The sample dispensing tip-reaction container holding member 107 installs the reaction container 105 and the sample dispensing tip which are unused, at multiple locations. The above-described sample dispensing tip-reaction container transporting mechanism 106 moves upward from the sample dispensing tip-reaction container holding member 107, descends and ascends while gripping the unused reaction container 105, moves upward from a predetermined position of the incubator disc 104, and descends so as to install the reaction container 105 in the incubator disc 104. In addition, the sample dispensing tip-reaction container transporting mechanism 106 moves upward from the sample dispensing tip-reaction container holding member 107, descends and ascends while gripping the unused sample dispensing tip, moves upward from the sample dispensing tip mounting position 110, and descends so as to install the sample dispensing tip at the sample dispensing tip mounting position 110.

The sample dispensing device 103 is configured to pivot and vertically move a dispensing nozzle (not illustrated), and pivots, moves, and lays down the dispensing nozzle above the sample dispensing tip mounting position 110, thereby mounting the sample dispensing tip on a distal end of the dispensing nozzle in a press-fitting manner. The dispensing nozzle having the sample dispensing tip mounted thereon moves upward from the sample container 102 placed on the rack 101, and descends so as to aspirate a predetermined amount of the sample held by the sample container 102. The dispensing nozzle aspirating the sample moves upward from the incubator disc 104, and descends so as to discharge the sample to the unused reaction container 105 held by the incubator disc 104. If the sample is completely discharged, the dispensing nozzle moves upward from the sample dispensing tip-reaction container discarding hole 109 so as to discard the used sample dispensing tip through the sample dispensing tip-reaction container discarding hole 109.

The multiple reagent containers 118 are installed in the reagent disc 111. A reagent disc cover 112 (FIG. 1 is a view obtained by partially breaking a left portion) is disposed in an upper portion of the reagent disc 111. The inside of the reagent disc 111 is warmed up to predetermined temperature. An opening portion 113 is disposed in a portion on the incubator disc 104 side in the reagent disc cover 112.

The reagent dispensing device 114 may adopt a configuration in which the dispensing nozzle 122 (refer to FIG. 2) is horizontally moved in one axial direction. However, the present embodiment adopts a configuration in which the dispensing nozzle 122 is rotated and vertically moved similarly to the sample dispensing device 103. The reagent dispensing device 114 rotates, moves, and lays down the dispensing nozzle 122 above the opening portion 113 of the reagent disc cover 112. The reagent dispensing device 114 inserts the distal end of the dispensing nozzle 122 into a predetermined reagent container 118 so as to aspirate a predetermined amount of reagent. In this case, in the reagent disc 111, the reagent to be aspirated by the dispensing nozzle 122 is moved in advance to a position below the opening portion 113. In addition, a liquid level sensor 121 (refer to FIG. 2) using electrostatic capacitance is provided for the reagent dispensing device 114. When the reagent is aspirated, a descending amount of the dispensing nozzle 122 is controlled so as to minimize a portion of the dispensing nozzle 122 dipped into the reagent (for example, a dipping amount which enables only a necessary amount of the reagent to be aspirated). After the reagent is aspirated, the dispensing nozzle 122 ascends, rotates, and moves upward from a predetermined position of the incubator disc 104 so as to discharge the reagent to the reaction container 105. Thereafter, before proceeding to the next reagent aspirating process, the dispensing nozzle 122 rotates and moves upward from the cleaning tank so as to be cleaned.

The reaction container 105 to which the sample and the reagent are discharged moves to a predetermined position in response to the rotation of the incubator disc 104, and is transported to a place of the reaction container stirring mechanism 108 by the sample dispensing tip-reaction container transporting mechanism 106. The reaction container stirring mechanism 108 adds a rotational motion to the reaction container 105, thereby stirring and mixing the sample and the reagent with each other inside the reaction container 105. The completely stirred reaction container 105 is caused to return to a predetermined position in the incubator disc 104 by the sample dispensing tip-reaction container transporting mechanism 106.

The reaction container transporting mechanism 115 can rotate and vertically move similarly to the sample dispensing device 103, and moves upward from the reaction container 105 in which a predetermined reaction period of time elapses after the sample and the reagent are completely dispensed and stirred, and which are caused to return to the incubator disc 104. The reaction container transporting mechanism 115 descends and ascends while gripping the reaction container 105 so as to transport the reaction container 105 to the detection unit 116 by using the rotational movement. According to the present embodiment, the detection unit 116 and the reaction container transporting mechanism 115 are disposed two by two, thereby doubling analysis processing efficiency through parallel analysis.

A process performed by the above-described respective devices and a nozzle cleaning operation to be described below are performed by the control device 120.

2. Configuration of Reagent Nozzle Cleaning Tank

Figure 2:
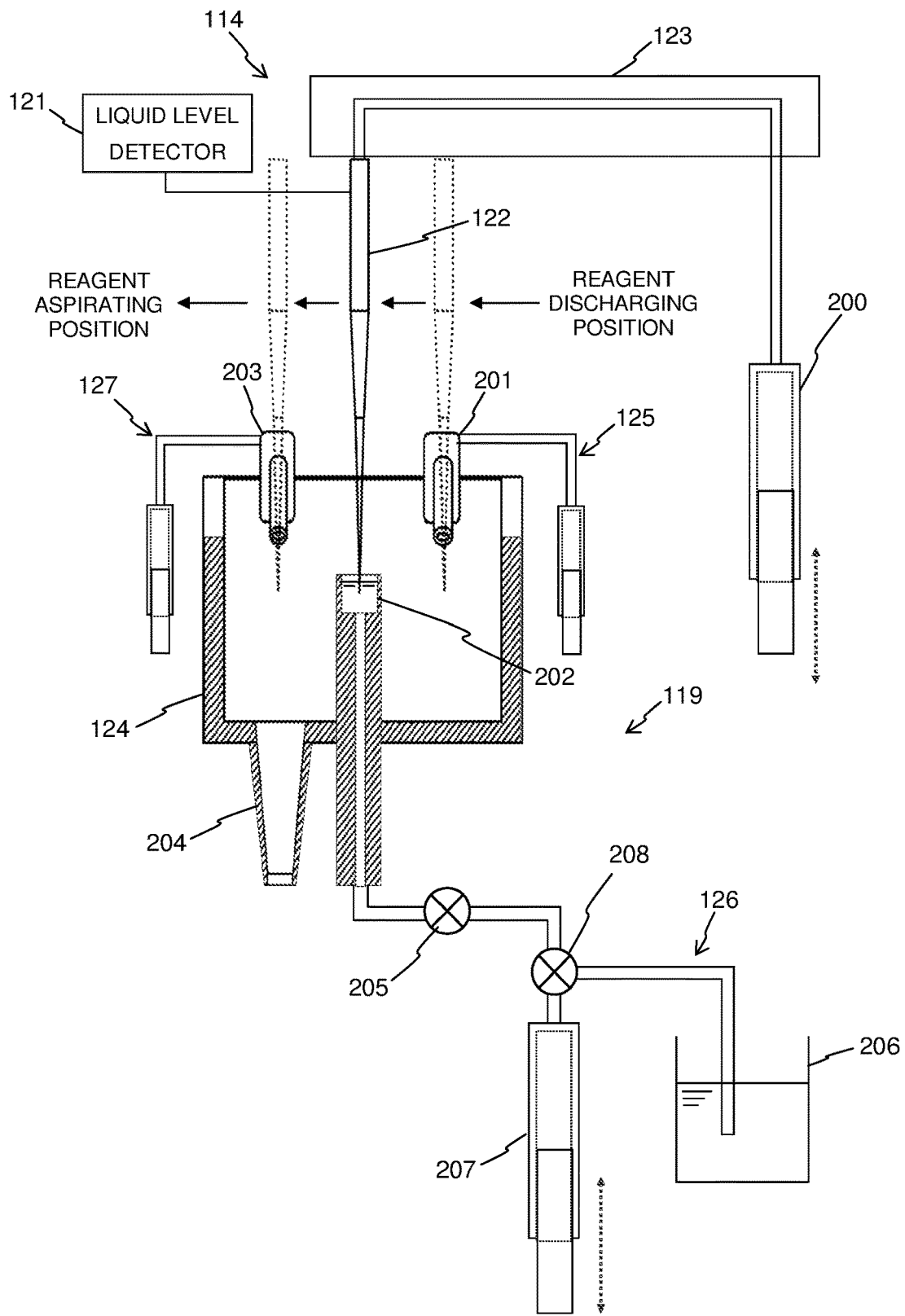
FIG. 2 schematically illustrates a reagent dispensing device and a nozzle cleaning device which are included in an automatic analysis device according to a first embodiment of the present invention.

FIG. 2 schematically illustrates the reagent dispensing device 114 and the nozzle cleaning device 119.

The reagent dispensing device 114 includes a dispensing nozzle (probe) 122, a moving device 123, a dispensing syringe 200, and a liquid level detector 121. The moving device 123 includes an arm whose one end is linked to a vertical shaft. One drive device (not illustrated) pivots the arm so that the dispensing nozzle 122 vertically disposed in the other end of the arm rotates and moves around the shaft, and the other drive device (not illustrated) vertically moves the arm so that the dispensing nozzle 122 vertically moves. The dispensing syringe 200 is connected to the dispensing nozzle 122, thereby causing the dispensing nozzle 122 to aspirate the reagent or causing the dispensing nozzle 122 to discharge the reagent. A pre-compression solution is aspirated in the dispensing syringe 200 and a conduit line which connects the dispensing syringe 200 and the dispensing nozzle 122 to each other.

The liquid level detector 121 is connected to the dispensing nozzle 122, and detects the presence of the reagent or the cleaning solution via the dispensing nozzle 122 by electrostatic capacitance. For example, if the dispensing nozzle 122 comes into contact with the reagent or the cleaning solution, the liquid level detector 121 detects the presence of the reagent or the cleaning solution. Although not particularly described herein, the sample dispensing device 103 also has the same basic configuration as the reagent dispensing device 114.

The nozzle cleaning device 119 includes a cleaning tank 124, a first cleaning solution discharge port 201, a second cleaning solution storage tank 202, a third cleaning solution discharge port 203, a first cleaning solution supply unit 125, a second cleaning solution supply unit 126, and a third cleaning solution supply unit 127.

The cleaning tank 124 is arranged on the trajectory of the dispensing nozzle 122 between the incubator disc 104 and the reagent disc 111. The cleaning tank 124 is a container for performing a first cleaning step, a second cleaning step, and a third cleaning step (to be described later) on the dispensing nozzle 122. The above-described first cleaning solution discharge port 201, second cleaning solution storage tank 202, and third cleaning solution discharge port 203 are respectively disposed at first to third cleaning positions inside the cleaning tank 124. In addition, a discharge port 204 is disposed in a bottom portion of the cleaning tank 124. The discharge port 204 may be disposed at multiple locations.

The first cleaning position, the second cleaning position, and the third cleaning position are arrayed in this order from the incubator disc 104 (reagent dispensing position) toward the reagent disc 111 (reagent aspirating position) on the trajectory of the dispensing nozzle 122. In the drawing, a position where the dispensing nozzle 122 is illustrated by a solid line represents the second cleaning position, a position where the dispensing nozzle 122 is illustrated by a broken line on the right side of the second cleaning position represents the first cleaning position, and a position where the dispensing nozzle 122 is illustrated by a broken line on the left side of the second cleaning position represents the third cleaning position.

At the first cleaning position, a first cleaning solution discharged from the first cleaning solution discharge port 201 via the first cleaning solution supply unit 125 is applied to the outer wall surface of the dispensing nozzle 122 located at the first cleaning position. At the third cleaning position, a third cleaning solution discharged from the third cleaning solution discharge port 203 via the third cleaning solution supply unit 127 is applied to the outer wall surface of the dispensing nozzle 122 located at the third cleaning position. According to the present embodiment, the first and third cleaning solution discharge ports 201 and 203 are disposed one by one at a position which does not hinder the movement of the dispensing nozzle 122. The second cleaning position is located between the first cleaning position and the third cleaning position.

The second cleaning solution storage tank 202 is disposed at the second cleaning position, and the second cleaning solution supply unit 126 for supplying a second cleaning solution is connected to the second cleaning solution storage tank 202. The second cleaning solution supply unit 126 includes a tank 206, a liquid feeding syringe 207, a channel switching valve 208, and an electromagnetic valve 205. The liquid feeding syringe 207 is connected to the tank 206 via a conduit line. The conduit line for connecting the tank 206 and the liquid feeding syringe 207 to each other is bifurcated and connected to the second cleaning solution storage tank 202. The channel switching valve 208 is disposed in a bifurcated portion of the conduit line, and the electromagnetic valve 205 is disposed in the conduit line for connecting the channel switching valve 208 and the second cleaning solution storage tank 202 to each other. The channel switching valve 208 causes a connection partner of the liquid feeding syringe 207 to be switched to either the tank 206 or the second cleaning solution storage tank 202. The liquid feeding syringe 207 in a state of being connected to the tank 206 via the channel switching valve 208 aspirates the second cleaning solution, the connection partner is switched to the second cleaning solution storage tank 202, and the liquid feeding syringe 207 discharges the second cleaning solution. In this manner, the second cleaning solution is supplied to the second cleaning solution storage tank 202. The electromagnetic valve 205, the channel switching valve 208, and the liquid feeding syringe 207 are operated in accordance with a signal output from the control device 120.

Similarly, the first cleaning solution supply unit 125 and the third cleaning solution supply unit 127 which respectively supply the first cleaning solution and the third cleaning solution to the first cleaning solution discharge port 201 and the third cleaning solution discharge port 203 are connected to the first cleaning solution discharge port 201 and the third cleaning solution discharge port 203. A conduit line structure through which the first cleaning solution discharge unit 125 and the third cleaning solution discharge unit 127 supply the cleaning solution is the same as that of the second cleaning solution supply unit 126. Thus, both of these are simplified in the illustration, and description thereof will be omitted. However, similarly, a syringe for supplying the cleaning solution is connected to the first cleaning solution discharge port 201 and the third cleaning solution discharge port 203 via a conduit line. In addition, as the first to third cleaning solutions, all different cleaning solutions can be used, but at least two cleaning solutions can employ the same cleaning solution.

3. Cleaning Procedure

Figure 7:
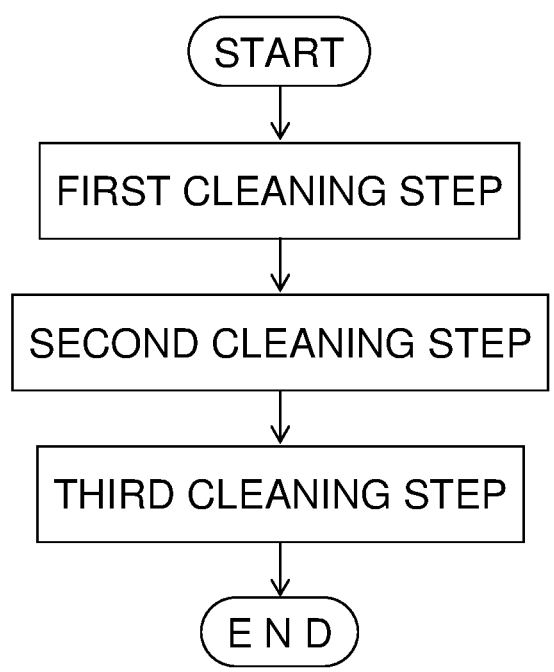
FIG. 7 is a flowchart illustrating a cleaning procedure of a dispensing nozzle which is controlled by a control device included in the automatic analysis device according to the first embodiment of the present invention.

FIG. 7 is a flowchart illustrating a cleaning procedure of the dispensing nozzle which is controlled by the control device 120.

As illustrated in the drawing, the cleaning process of the dispensing nozzle includes three steps of a first cleaning step, a second cleaning step, and a third cleaning step. The control device 120 controls the reagent dispensing device 114 and the nozzle cleaning device 119 so as to perform the first to third cleaning steps. The first to third cleaning steps will be respectively described.

(1) First Cleaning Step

In the first cleaning step, after causing the reaction container 105 on the incubator disc 104 to discharge the reagent, the control device 120 outputs a signal to the moving device 123 so as to move the dispensing nozzle 122 to the first cleaning position. Then, the control device 120 outputs a signal to the dispensing syringe 200 and the first cleaning solution supply unit 125, and drives the dispensing syringe 200 so as to discharge a pre-compression solution through the dispensing nozzle 122. The control device 120 drives the syringe of the first cleaning solution supply unit 125 so as to apply the first cleaning solution to the outer wall surface of the dispensing nozzle 122. That is, the pre-compression solution is discharged, thereby cleaning the inner wall surface of the dispensing nozzle 122. The first cleaning solution is applied, thereby cleaning the outer wall surface of the dispensing nozzle 122. In the cleaning of the inner wall surface and the cleaning of the outer wall surface of the dispensing nozzle 122 in the first cleaning step, any cleaning may be performed earlier, or both of these may be performed at the same time. The first cleaning solution applied to the outer wall surface of the dispensing nozzle 122 at the first cleaning position is received by the cleaning tank 124, and is discharged to a liquid discharge tank (not illustrated) from the cleaning tank 124 via the discharge port 204.

(2) Second Cleaning Step

If the procedure proceeds to the second cleaning step after the first cleaning step is completed, the control device 120 outputs a signal to the moving device 123 so as to move the dispensing nozzle 122 to the second cleaning position and to dip a distal end of the dispensing nozzle 122 into the second cleaning solution. In this case, during the second cleaning solution aspirating operation in the second cleaning step, the control device 120 controls the height of the distal end of the dispensing nozzle 122 so as to be the height which enables only a necessary amount of the second cleaning solution to be aspirated. The "height which enables only a necessary amount of the second cleaning solution to be aspirated" means a height position which is lowered from the liquid level of the second cleaning solution by a volume amount corresponding to the necessary amount of the second cleaning solution, if the liquid level height of the second cleaning solution cannot be maintained constant (if the second cleaning solution is not supplied concurrently with the aspirating) when the second cleaning solution is aspirated, and means a height position of the liquid level of the second cleaning solution (or a height position which is lowered from the liquid level by a minimum necessary nozzle dipping amount during the aspirating operation), if the liquid level height of the second cleaning solution can be maintained constant (if the second cleaning solution is supplied concurrently with the aspirating) when the second cleaning solution is aspirated. If the dispensing nozzle 122 is moved to the second cleaning position in this way, the control device 120 outputs a signal to the dispensing syringe 200 so that the dispensing nozzle 122 aspirates the second cleaning solution, thereby cleaning the inner wall surface of the dispensing nozzle 122.

In this case, in accordance with the second cleaning solution of the second cleaning solution storage tank 202 which is decreased by performing the second cleaning step, the control device 120 outputs a signal to the second cleaning solution supply unit 126 so as to supplement the second cleaning solution to the second cleaning solution storage tank 202. This procedure may be performed after the second cleaning step is performed by the time the subsequent second cleaning step starts. However, for example, the dispensing syringe 200 and the second cleaning solution supply unit 126 are controlled while the second cleaning step is performed. The dispensing nozzle 122 aspirates the second cleaning solution, and concurrently the second cleaning solution supply unit 126 supplies the cleaning solution to the second cleaning solution storage tank 202. In this manner, the liquid level of the second cleaning solution may be maintained in the second cleaning solution storage tank 202.

In addition, in the second cleaning step, the control device 120 controls the dispensing syringe 200. Accordingly, the distal end portion of the dispensing nozzle 122 is dipped into the second cleaning solution, deeply more than the height which enables only a necessary amount of the second cleaning solution to be aspirated (described above). In this manner, when the second cleaning solution is aspirated, the outer wall surface of the dispensing nozzle 122 can also be cleaned together. The amount dipped into the second cleaning solution in this case represents a value which is set in advance so that a portion to which a cleaning target including the reagent is supposed to adhere on the outer wall surface of the dispensing nozzle 122 is dipped into the second cleaning solution.

In addition, if necessary, during the second cleaning solution aspirating operation in the second cleaning step, the control device 120 maintains the height of dispensing nozzle 122, and dips the distal end portion of the dispensing nozzle 122 into the second cleaning solution. In this state, the control device 120 can output a signal to the dispensing syringe 200 so as to repeatedly aspirate and discharge the second cleaning solution.

(3) Third Cleaning Step

If the procedure proceeds to the third cleaning step after the second cleaning step is completed, the control device 120 outputs a signal to the moving device 123 so as to move the dispensing nozzle 122 to the third cleaning position, and outputs a signal to the dispensing syringe 200 and the third cleaning solution supply unit 127 so as to clean the inner wall surface of the dispensing nozzle 122 by discharging the second cleaning solution through the dispensing nozzle 122. The third cleaning solution is applied to the outer wall surface of the dispensing nozzle 122, so as to clean the outer wall surface of the dispensing nozzle 122. In this step, a schematic operation for discharging the second cleaning solution and causing the third cleaning solution to flow downward is similar to a schematic operation for discharging the pre-compression solution and causing the first cleaning solution to flow downward in the first cleaning step, except that a control target device for applying the cleaning solution to the dispensing nozzle 122 is changed from the first cleaning solution supply unit 125 to the third cleaning solution supply unit 127. In the cleaning of the inner wall surface and the cleaning of the outer wall surface of the dispensing nozzle 122 in the third cleaning step, any cleaning may be performed earlier, or both of these may be performed at the same time. The third cleaning solution applied to the outer wall surface of the dispensing nozzle 122 at the third cleaning position is received by the cleaning tank 124, and is discharged to a liquid discharge tank (not illustrated) from the cleaning tank 124 via the discharge port 204.

In addition, the control device 120 controls at least any one of the dispensing syringe 200 and the moving device 123, thereby holding the second cleaning solution aspirated in the second cleaning step inside the dispensing nozzle 122 during a set period of time. Accordingly, it is possible to further improve a cleaning effect of the inner wall surface of the dispensing nozzle 122. The "set period of time" described herein means a preset period of time which is added to a period of time during which the second cleaning solution stays inside the dispensing nozzle 122 when the second cleaning solution aspirating operation, the moving operation to the third cleaning position, and the second cleaning solution discharging operation are continuously performed in the second cleaning step at normal speed. Specifically, for example, the third cleaning step can be performed by at least one operation of delaying the movement speed from the second cleaning position to the third cleaning position, delaying the timing to discharge the second cleaning solution after arriving at the third cleaning position, and delaying the timing to move from the second cleaning position to the third cleaning position after the second cleaning solution is aspirated.

In at least any one of the above-described first to third cleaning steps, the liquid level detector 121 is used so as to detect the cleaning solution. Accordingly, it is possible to determine whether a discharging state or a storing state of the cleaning solution is normal. For example, based on a signal input from the liquid level detector 121, the control device 120 confirms that the cleaning solution is in contact with the dispensing nozzle 122. When the control device 120 cannot confirm that all of the first to third cleaning steps are normally performed, the control device 120 can output a signal for giving a notification of the cleaning step which is not normally performed, to an output device such as a display device, a sound device, and a printing device. In addition, if necessary, the control device 120 can also output a signal for giving a notification indicating that the first to third cleaning steps are normally performed, to the output device such as the display device, the sound device, and the printing device.

4. Advantageous Effect (1) Preventing Carryover

According to the present embodiment, when the inner wall surface of the dispensing nozzle 122 is cleaned by discharging the pre-compression solution in the first cleaning step before the second cleaning solution is aspirated, the outer wall surface is cleaned by the first cleaning solution. Even after the second cleaning solution is aspirated, the second cleaning solution is discharged in the third cleaning step, and the outer wall surface of the dispensing nozzle 122 is cleaned by the third cleaning solution. Therefore, even though the second cleaning solution is not brought into an overflowing state in the second cleaning solution storage tank 202, it is possible to prevent carryover when the dispensing nozzle 122 is dipped into the reagent in the second cleaning solution storage tank 202. In this manner, it is possible to minimize cleaning solution usage needed to clean the inner wall surface of the dispensing nozzle 122. Accordingly, it is possible to prevent carryover or contamination while the cleaning solution is prevented from being uselessly consumed. Therefore, not only the cost but also the frequently replaced consumables can be reduced.

(2) Efficiency 1 in Cleaning Process

As described above, the first to third cleaning positions are arrayed in this order from the reagent dispensing position toward the reagent aspirating position. Accordingly, it is possible to prevent a wasteful operation of the dispensing nozzle 122, since the dispensing nozzle 122 does not need to return to the reagent dispensing position side as the cleaning process advances. Therefore, the cleaning process can be efficiently performed. Moreover, it is possible to improve processing speed for sample analysis.

(3) Efficiency 2 in Cleaning Process

In at least any one of the first to third cleaning steps, when the cleaning processes are concurrently performed on the inner wall surface and the outer wall surface of the dispensing nozzle 122, it is possible to efficiently perform the cleaning process by shortening a period of time required for the cleaning process.

(4) Improvement 1 in Cleaning Effect

In the second cleaning step, when the dispensing nozzle 122 is dipped into the second cleaning solution, deeply more than the height which enables only a necessary amount of the second cleaning solution to be aspirated, compared to a case where the second cleaning solution is used only in cleaning the inner wall surface of the dispensing nozzle 122, the outer wall surface of the dispensing nozzle 122 can be cleaned together when the second cleaning solution is aspirated. Therefore, the further improved cleaning effect of the outer wall surface of the dispensing nozzle 122 can be expected.

(5) Improvement 2 in Cleaning Effect

During the second cleaning solution aspirating operation in the second cleaning step, when the dispensing nozzle 122 repeatedly aspirates and discharges the second cleaning solution, the further improved cleaning effect of the inner wall surface of the dispensing nozzle 122 can be expected.

(6) Improvement 3 in Cleaning Effect

When a state where the dispensing nozzle 122 aspirates the second cleaning solution is held during the set period of time, the further improved cleaning effect of the inner wall surface of the dispensing nozzle 122 can also be expected.

(7) Improved Reliability

If the liquid level detector 121 can be used so as to determine whether or not the cleaning process is normally performed, an operator can be quickly informed of a defective cleaning process. Therefore, the operator can quickly deal with a failure of each device such as the dispensing syringe 200 and the cleaning solution supply units 125 to 127, or a shortage of the cleaning solution, thereby contributing to carryover prevention.

(8) Simplified Device

If at least two of the first to third cleaning solutions are set to be the same cleaning solution, the cleaning solution tank or the conduit line can be shared in common, thereby enabling the device to be simplified. In addition, types of the cleaning solution are arranged in order, thereby facilitating the management.

For example, when a detergent having a high cleaning effect for the reagent is used as the second cleaning solution which is stored in the second cleaning solution storage tank 202 so as to clean the inner wall surface of the dispensing nozzle 122, and when a versatile liquid such as pure water and deionized water is shared in common as the first cleaning solution and the third cleaning solution, it is possible to minimize the consumption of the most expensive second cleaning solution as described above, thereby contributing to cost reduction. Even if the second cleaning solution having the high cleaning effect adheres to the outer wall surface of the dispensing nozzle 122 after the second cleaning step, the second cleaning solution can be easily washed off by the pure water or the deionized water in the third cleaning step. Therefore, it is possible to prevent carryover of the second cleaning solution having the high cleaning effect to the reagent.

5. Others

In the present embodiment, in order to achieve the above-described advantageous effect (2), a case where the first to third cleaning positions are arrayed in this order along the trajectory of the dispensing nozzle 122 has been described as an example. However, as long as the essential effect (1) can be achieved, the arrayed order of the first to third cleaning positions is not particularly limited. In addition, in order to achieve the above-described advantageous effect (3), a case where in at least any one of the first to third cleaning steps, the cleaning processes are concurrently performed on the inner and outer wall surfaces of the dispensing nozzle 122 has been described as an example. However, as long as the essential effect (1) can be achieved, the cleaning processes do not necessarily need to be concurrently performed on the inner and outer wall surfaces of the dispensing nozzle 122 in the first and third cleaning steps.

In addition, in order to achieve the above-described advantageous effect (4), a case where in the second cleaning step, the dispensing nozzle 122 is dipped into the second cleaning solution, deeply more than normal has been described as an example. However, as long as the essential effect (1) can be achieved, it is not necessarily required to follow this example. In addition, in order to achieve the above-described advantageous effect (5), a case where in the second cleaning step, the second cleaning solution is repeatedly aspirated and discharged has been described as an example. However, as long as the essential effect (1) can be achieved, this procedure can also be omitted. In order to achieve the above-described advantageous effect (6), a case where the second cleaning solution is held inside the dispensing nozzle 122 during the set period of time has been described as an example. However, as long as the essential effect (1) can be achieved, this procedure can also be omitted.

In order to achieve the above-described advantageous effect (7), a case where the liquid level detector 121 is used so as to detect whether the cleaning process is normally performed has been described as an example. However, as long as the essential effect (1) can be achieved, it is not necessarily required that the liquid level detector 121 is provided with a function to determine whether or not the cleaning process is normally performed.

Second Embodiment

Figure 3:
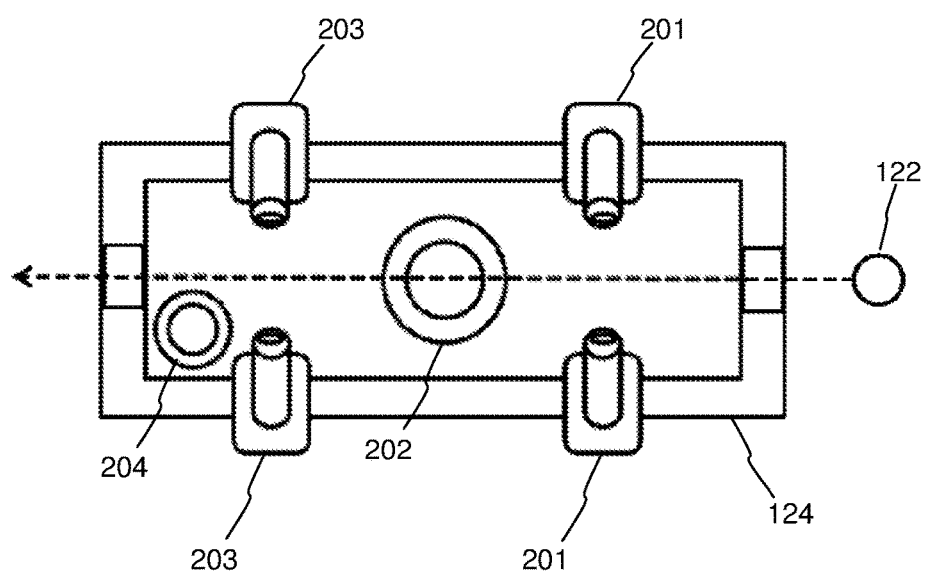
FIG. 3 is a plan view illustrating a configuration of a cleaning tank included in an automatic analysis device according to a second embodiment of the present invention.

FIG. 3 is a plan view illustrating a cleaning tank included in an automatic analysis device according to a second embodiment of the present invention.

A point different from that according to the first embodiment is that the first to third cleaning solutions are applied from both sides of the dispensing nozzle 122. In the first embodiment, each number of the first and third cleaning solution discharge ports 201 and 203 is not particularly described. The number of the first cleaning solution discharge ports 201 may be one. However, a configuration can also be adopted in which two first cleaning solution discharge ports 201 are arranged to face each other across the trajectory of the dispensing nozzle 122 as in the present embodiment. That is, the first cleaning solutions discharged from the two first cleaning solution discharge ports 201 are controlled to collide with each other near the first cleaning position. In this manner, a configuration is adopted in which the two first cleaning solution discharge ports 201 apply the first cleaning solution to the dispensing nozzle 122 located at the first cleaning position in two direction which are opposite to each other. In addition, as long as the movement of the dispensing nozzle 122 is not hindered, three or more first cleaning solution discharge ports 201 may be disposed. This point is similarly applied to the third cleaning solution discharge port 203. That is, the number of the first and third cleaning solution discharge ports 201 and 203 may be one. However, at least any one can be disposed at multiple locations. Other points according to the present embodiment are the same as those according to the first embodiment.

According to the present embodiment, in addition to the same advantageous effect as that according to the first embodiment, at least one of the first and third cleaning solutions is applied to the dispensing nozzle 122 through the multiple discharge ports. Therefore, it is possible to efficiently clean the entire periphery of the outer wall surface of the dispensing nozzle 122.

Third Embodiment

Figure 4:
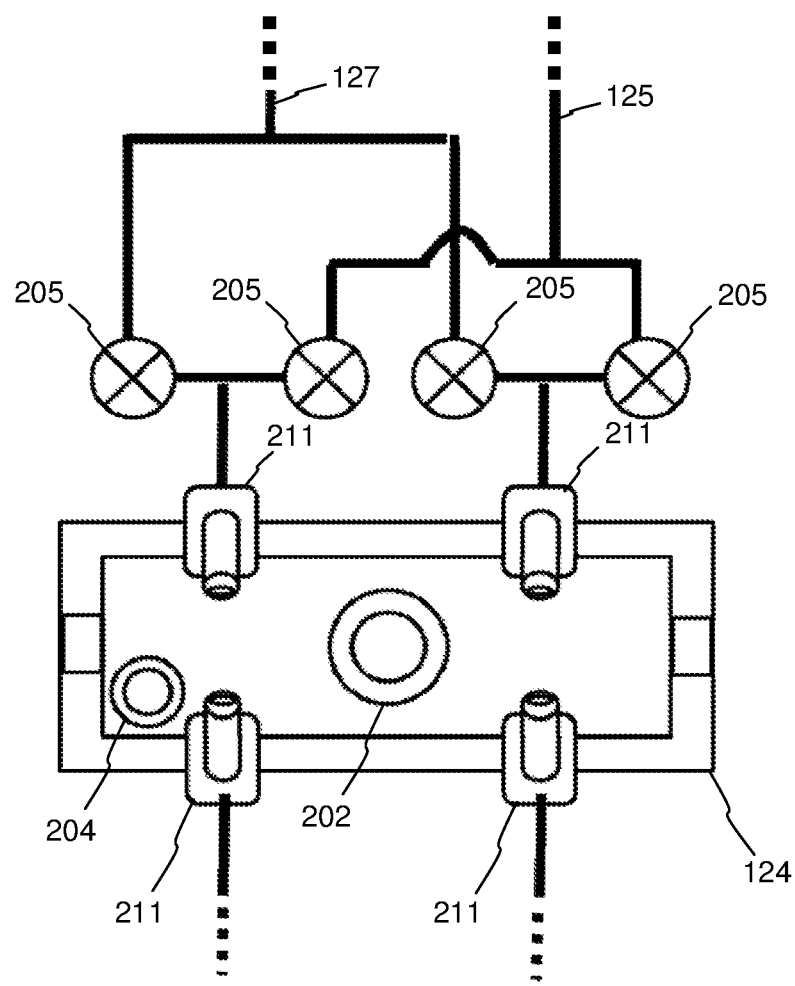
FIG. 4 is a schematic view of a nozzle cleaning device included in an automatic analysis device according to a third embodiment of the present invention.

FIG. 4 is a schematic view of the nozzle cleaning device included in an automatic analysis device according to a third embodiment of the present invention.

The nozzle cleaning device 119 illustrated in the drawing includes a common cleaning solution discharge port 211 at the position of the first and third cleaning solution discharge ports 201 and 203 according to the second embodiment. The common cleaning solution discharge port 211 is a cleaning solution discharge port shared in common in order to discharge the first and third cleaning solutions. Specifically, the first cleaning solution supply unit 125 and the third cleaning solution supply unit 127 are connected to the common cleaning solution discharge port 211 via the electromagnetic valve 205. The electromagnetic valve 205 is operated by a signal output from the control device 120, and switches a connection target of the common cleaning solution discharge port 211 to either the first cleaning solution supply unit 125 or the third cleaning solution supply unit 127. In this manner, the first cleaning solution or the third cleaning solution is discharged from the common cleaning solution discharge port 211. Other configurations according to the present embodiment are the same as those according to the second embodiment, and thus, the same advantageous effects as those according to the above-described two embodiments can be achieved.

In addition, in FIG. 4, a case where the common cleaning solution discharge ports 211 are arranged two by two (four in total) at the first and the second cleaning positions by following the example according to the second embodiment has been described as an example. However, since the common cleaning solution discharge port 211 can selectively discharge both the first and third cleaning solution, the first cleaning position and the third cleaning position can be shared with each other. A configuration is adopted in which the first cleaning step is performed at the common cleaning position in the first and third cleaning steps, the second cleaning step is performed by moving to the second cleaning position, and thereafter the third cleaning step is performed by returning to the common cleaning position. In this case, the number of the common cleaning solution discharge ports 211 may be at least one, thereby enabling a compact device configuration to be provided. For example, this configuration is effective when the first to third cleaning positions are not separately secured between the aspirating position and the discharging position of the dispensing nozzle 122.

On the other hand, if the common cleaning solution discharge port 211 is provided at two locations across the second cleaning solution storage tank 202, the cleaning process of the dispensing nozzle 122 can start in both directions on the reagent discharging position side and the reagent aspirating position side. Accordingly, without depending on a standby position of the dispensing nozzle 122 when the analysis starts or when the analysis restarts, the cleaning process of the dispensing nozzle 122 can be performed by using a short route.

In addition, when it is, necessary to repeatedly perform the first to third cleaning steps, the present embodiment is efficient, since the third cleaning step and the subsequent first cleaning step can be continuously performed at the same cleaning position.

Fourth Embodiment

Figure 5:
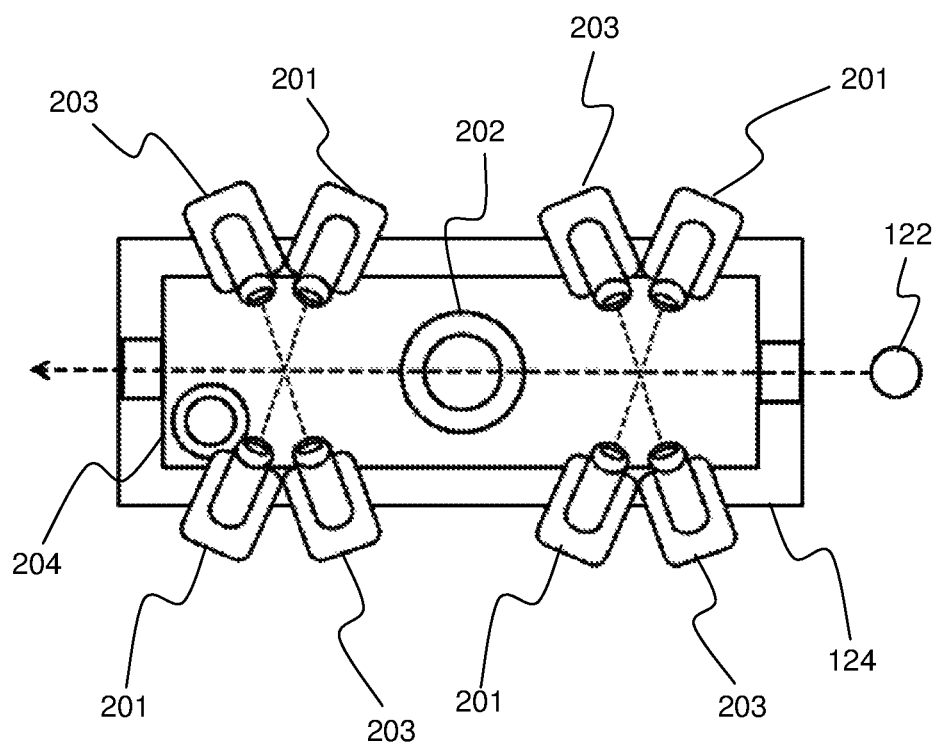
FIG. 5 is a plan view of a cleaning tank included in an automatic analysis device according to a fourth embodiment of the present invention.

FIG. 5 is a plan view of a cleaning tank included in an automatic analysis device according to a fourth embodiment of the present invention.

As illustrated in the drawing, the present embodiment is common to the third embodiment in that the first and third cleaning positions are positions shared in common. However, the present embodiment is different from the third embodiment in that the common cleaning solution discharge port 211 does not selectively supply the first and third cleaning solutions, and that the first and third cleaning solution discharge ports 201 and 203 are disposed so as to discharge the first and third cleaning solutions toward the common position. In the present embodiment, a case where the first and third cleaning solution discharge ports 201 and 203 are respectively installed pair by pair on both sides across the second cleaning position has been described as an example. However, the first and third cleaning solution discharge ports 201 and 203 may be disposed at least one by one at any position. Other configurations according to the present embodiment are the same as those according to the third embodiment, and thus, the same advantageous effects as those according to the third embodiment can be achieved.

In addition, in a case of the present embodiment, the first and third cleaning solution flowing paths connected to the first and third cleaning solution discharge ports 201 and 203 can be completely divided. Accordingly, there is an advantage in that the first and third cleaning solutions can be prevented from being mixed with each other inside the path, while the benefit can be enjoyed owing to the configuration in which the first and third cleaning solutions are supplied to the common position.

Fifth Embodiment

Figure 6A:
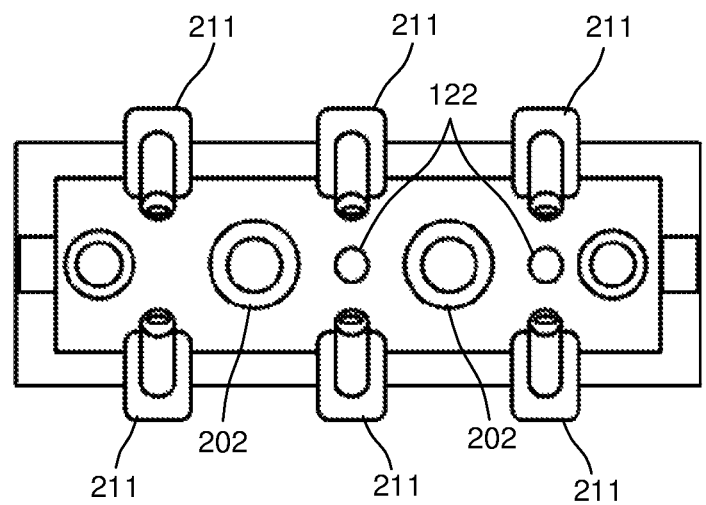
FIG. 6A is a plan view when a first cleaning step is performed in a cleaning tank included in an automatic analysis device according to a fifth embodiment of the present invention.
Figure 6B:
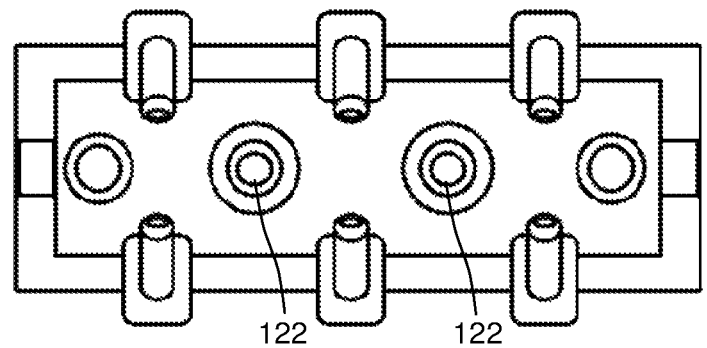
FIG. 6B is a plan view when a second cleaning step is performed in the cleaning tank included in the automatic analysis device according to the fifth embodiment of the present invention.
Figure 6C:
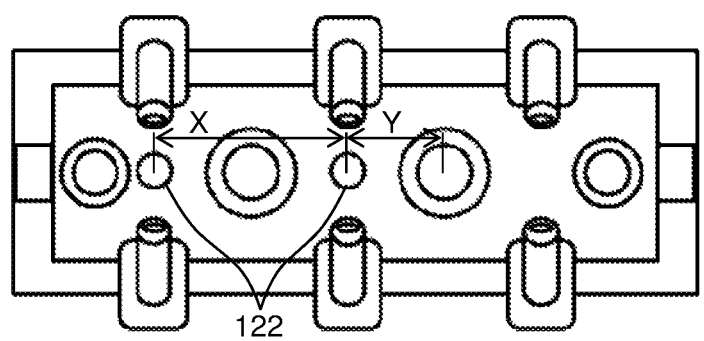
FIG. 6C is a plan view when a third cleaning step is performed in the cleaning tank included in the automatic analysis device according to the fifth embodiment of the present invention.

FIGS. 6A to 6C are plan views of a cleaning tank included in an automatic analysis device according to a fifth embodiment of the present invention.

A point different from that according to the above-described respective embodiments is that multiple dispensing nozzles 122 are supposed to be concurrently cleaned. Specifically, a common cleaning position serving as the first and third cleaning positions, and the second cleaning position are arranged at multiple locations at mutually equal intervals along the movement route of the dispensing nozzle 122, and a pair of the above-described common cleaning solution discharge ports 211 are arranged at the common cleaning position so as to face each other. The second cleaning solution storage tank 202 is arranged at the second cleaning position. In the example illustrated in FIG. 6, the common cleaning position is disposed at three locations, and the second cleaning position is disposed at two locations. In addition, multiple (two in the present embodiment) dispensing nozzles 122 are included in the reagent dispensing device 114. An interval between the multiple dispensing nozzles 122 is set to be equal to an interval between the common cleaning position and the second cleaning position which are adjacent to each other, or a multiple thereof (twice in the present embodiment). That is, the interval from the common cleaning position to the subsequent common cleaning position and the interval from the second cleaning position to the subsequent second cleaning position are equal to the interval between the dispensing nozzles 122. Then, the multiple dispensing nozzles 122 are sequentially moved along the arrangement of the cleaning positions disposed in this way. Accordingly, the first to third cleaning steps are respectively and concurrently performed on the multiple dispensing nozzles 122.

In FIG. 6, a reagent discharging position is located on the right side of the cleaning tank 124 and a reagent aspirating position is located on the left side. FIG. 6A illustrates the first cleaning step, FIG. 6B illustrates the second cleaning step, and FIG. 6C illustrates the third cleaning step. FIG. 6 illustrates a state where the first to third cleaning steps are respectively and concurrently performed on two dispensing nozzles 122. Specifically, the two dispensing nozzles 122 which have completely discharged the reagent are respectively moved to the right side and the central common cleaning position as illustrated in FIG. 6A so as to concurrently perform the first cleaning step. If the first cleaning step is completed, the two dispensing nozzles 122 are respectively moved to the left as illustrated in FIG. 6B, and are moved to the second cleaning position so as to concurrently perform the second cleaning step. After the second cleaning step is completed, the two dispensing nozzles 122 are respectively moved to the left side and the central cleaning solution discharging position so as to concurrently perform the third cleaning step. That is, according to the configuration illustrated in FIG. 6, the dispensing nozzle 122 on the left side performs the first cleaning step at the central cleaning solution discharging position, and the reagent dispensing nozzle 122 on the right side performs the third cleaning step. Both of these operations are performed as a result of the operations of the moving device 123, the dispensing syringe 200, and the first to third cleaning solution supply units 125 to 127 in accordance with signals output from the control device 120. Other configurations are the same as those according to the previously described embodiments, and thus, the above-described advantageous effect can be achieved.

In addition, in a case of the present embodiment, the second cleaning positions, the number of which is the same as the number of dispensing nozzles 122 and the common cleaning positions, the number of which is one more than the number of dispensing nozzles 122, are disposed. In this manner, the first to third cleaning steps can be concurrently performed on the multiple dispensing nozzles 122, from the reagent discharging position toward the reagent aspirating position, without causing the multiple dispensing nozzles 122 to return to the previous positions. Even when the number of dispensing nozzles 122 further increases, the second cleaning positions and the common cleaning positions are arrayed from the reagent discharging position toward the reagent aspirating position at an equal interval Y (=interval X between the dispensing nozzles 122 or its submultiple). In this manner, the same cleaning process can be concurrently performed on the respective dispensing nozzles 122. The above-described intervals X and Y and the interval Y are expressed by the following equation.

$$X = nY \text{ ($n$ is an arbitrary integer)}$$

For example, FIG. 6 illustrates a case of n=2 (X=2Y).

However, unless the same cleaning process is concurrently performed on the multiple dispensing nozzles 122, the multiple dispensing nozzles 122 can be concurrently cleaned, even when a configuration according to another embodiment (for example, FIG. 3) is adopted. That is, a form may be employed in which the interval between the dispensing nozzles 122 is set to be equal to the interval Y between the common cleaning position and the second cleaning position or multiple thereof, in which the multiple dispensing nozzles 122 are caused to sequentially perform the cleaning process, and in which when the preceding dispensing nozzle 122 is switched to perform the second or third cleaning step, the subsequent dispensing nozzle 122 starts the first cleaning step.

(Others)

In the above-described embodiments, a case where the invention is applied to the dispensing nozzle 122 of the reagent dispensing device 114 has been described as an example. However, the present invention is also applicable to cleaning a dispensing nozzle of the sample nozzle dispensing device 103 for aspirating and discharging a sample such as blood and urine.

In addition, all of the dispensing nozzles 122 used in the automatic analysis device do not need to be a cleaning target. For example, when the dispensing nozzle 122 which is not used in the dispensing (does not need to be cleaned) passes through the nozzle cleaning device 119, the dispensing nozzle 122 which is not used in the dispensing is allowed to omit one or all of the first to third cleaning steps. Accordingly, it is possible to minimize the consumption of the cleaning solution.

Figure 8:
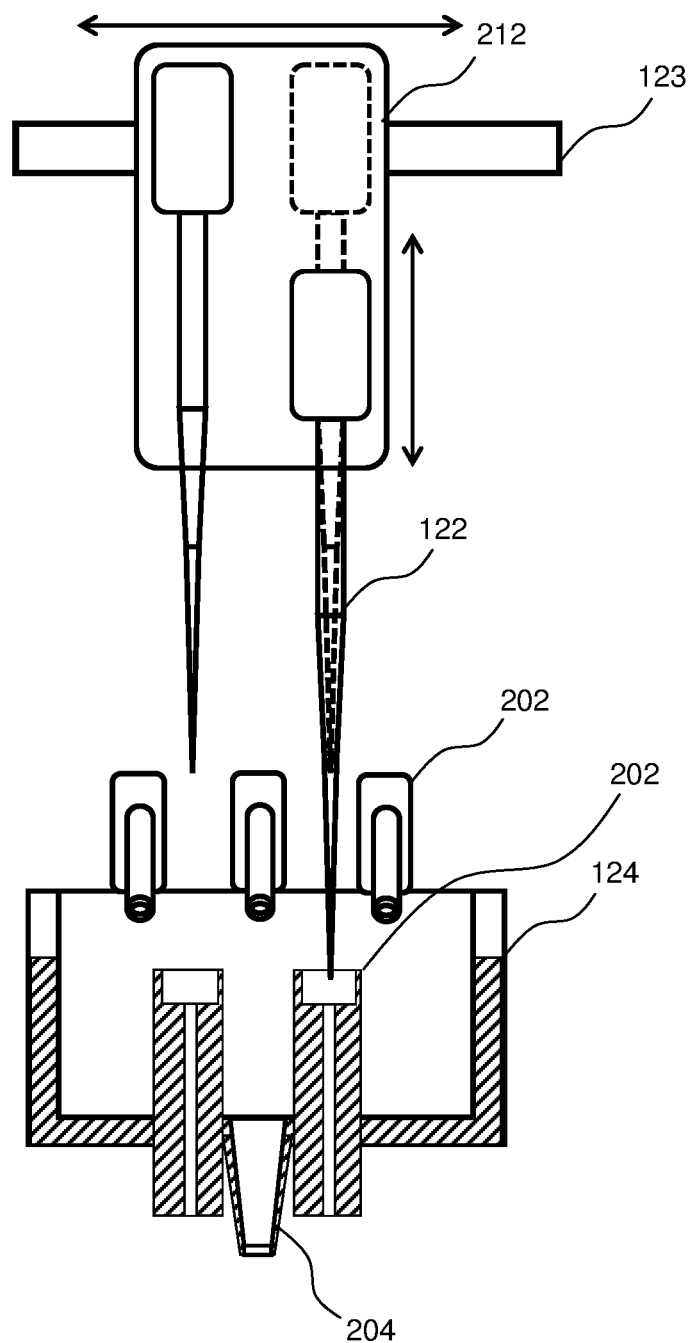
FIG. 8 illustrates a structure of independently and vertically movable dispensing probe included in an automatic analysis device according to another embodiment of the present invention.

As a technique for omitting each cleaning step, a method is conceivable in which the control device 120 controls the driving of the liquid feeding syringe so as not to discharge or supply cleaning water from any cleaning solution discharge port at which the dispensing nozzle which does not need to be cleaned is positioned or the cleaning solution storage tank. Alternatively, as illustrated in FIG. 8, when a vertical moving mechanism 212 which can independently and vertically move each dispensing nozzle is disposed in the moving device 123 for horizontally moving the dispensing nozzle, an upper stage movement route which does not pass through the first to third cleaning positions and a lower stage movement route which passes through the first to third cleaning positions are prepared in advance. The dispensing nozzle 122 which does not need to be cleaned (for example, before the dispensing) is not caused to descend in the direction toward the cleaning tank, and is moved by way of the upper stage movement route. Only the dispensing nozzle which needs to be cleaned (for example, after the dispensing) is moved by way of the lower stage movement route in order to perform the first to third cleaning steps. In this way, the control device 120 may control the moving device 123 so as to omit unnecessary cleaning steps.

REFERENCE SIGNS LIST

120 CONTROL DEVICE
121 LIQUID LEVEL DETECTOR
122 DISPENSING NOZZLE
123 MOVING DEVICE
124 CLEANING TANK
125 FIRST CLEANING SOLUTION SUPPLY UNIT
126 SECOND CLEANING SOLUTION SUPPLY UNIT
127 THIRD CLEANING SOLUTION SUPPLY UNIT
200 DISPENSING SYRINGE
201 FIRST CLEANING SOLUTION DISCHARGE PORT
202 SECOND CLEANING SOLUTION STORAGE TANK
203 THIRD CLEANING SOLUTION DISCHARGE PORT
207 LIQUID FEEDING SYRINGE
211 COMMON CLEANING SOLUTION DISCHARGE PORT
212 VERTICAL MOVING MECHANISM
Y INTERVAL BETWEEN COMMON CLEANING POSITION AND SECOND CLEANING POSITION
X INTERVAL BETWEEN DISPENSING NOZZLES

The invention claimed is:

1. A nozzle cleaning method consisting of:
a first cleaning step of cleaning an inner wall surface of a dispensing nozzle located at a first position in a cleaning tank by discharging a preloaded solution from the inside of the dispensing nozzle, and concurrently cleaning an outer wall surface of the dispensing nozzle located at the first position by discharging a cleaning solution from a pair of first discharge ports to the outer wall surface of the dispensing nozzle;
a second cleaning step of cleaning the inner wall surface of the dispensing nozzle located at a second position in the cleaning tank by aspirating the cleaning solution stored in a storage tank of the cleaning tank into the dispensing nozzle; and
a third cleaning step of cleaning the inner wall surface of the dispensing nozzle located at a third position in the cleaning tank by discharging the cleaning solution aspirated into the dispensing nozzle, and concurrently cleaning the outer wall surface of the dispensing nozzle located at the third position by discharging the cleaning solution from a pair of second discharge ports to the outer wall surface of the dispensing nozzle.

2. The nozzle cleaning method according to claim 1, wherein the dispensing nozzle includes a liquid level detector configured to detect the cleaning solution in at least one of the first to third cleaning steps, and wherein when the cleaning solution is not detected in the at least one of the first to third cleaning steps, a notification is output.

3. The nozzle cleaning method according to claim 1, wherein, in the second cleaning step, the dispensing nozzle is lowered into the cleaning solution, more deeply than a height for aspirating a predetermined amount of the cleaning solution, so as to clean the outer wall surface of the dispensing nozzle together when the cleaning solution is aspirated.

4. The nozzle cleaning method according to claim 1, wherein the cleaning solution aspirated in the second cleaning step is held inside the dispensing nozzle during a set period of time.

5. The nozzle cleaning method according to claim 1, wherein the cleaning solution is repeatedly aspirated and discharged in the second cleaning step.

6. The nozzle cleaning method according to claim 1, wherein the cleaning solution is discharged to the dispensing nozzle in multiple directions in the first and third cleaning steps.

* * * * *